United States Patent
Young (10) Patent No.: US 10,702,288 B2
(45) Date of Patent: Jul. 7, 2020

(54) ATTACHMENT MECHANISM FOR A SURGICAL INSTRUMENT COMPONENT

(71) Applicant: DEPUY IRELAND UNLIMITED COMPANY, County Cork (IE)

(72) Inventor: Duncan Young, Melbourn (GB)

(73) Assignee: DEPUY IRELAND UNLIMITED COMPANY (IE)

( * ) Notice: Subject to any disclaimer, the term of this patent is extended or adjusted under 35 U.S.C. 154(b) by 83 days.

(21) Appl. No.: 15/560,008

(22) PCT Filed: Feb. 3, 2016

(86) PCT No.: PCT/EP2016/052294
§ 371 (c)(1),
(2) Date: Sep. 21, 2017

(87) PCT Pub. No.: WO2016/150601
PCT Pub. Date: Sep. 29, 2016

(65) Prior Publication Data
US 2018/0064503 A1 Mar. 8, 2018

(30) Foreign Application Priority Data
Mar. 23, 2015 (GB) .................................. 1504854.9

(51) Int. Cl.
*A61B 17/16* (2006.01)

(52) U.S. Cl.
CPC ........ *A61B 17/1666* (2013.01); *A61B 17/162* (2013.01); *A61B 17/1631* (2013.01); *A61B 17/1633* (2013.01); *A61B 17/1622* (2013.01)

(58) Field of Classification Search
CPC ... A61B 17/16; A61B 17/1613; A61B 17/162; A61B 17/1622; A61B 17/1631; A61B 17/1633; A61B 17/1662; A61B 17/1664; A61B 17/1666
See application file for complete search history.

(56) References Cited

U.S. PATENT DOCUMENTS

| | | | |
|---|---|---|---|
| 1,726,012 A * | 8/1929 | Bilz | B25C 1/02 227/147 |
| 5,601,560 A * | 2/1997 | Del Rio | A61B 17/162 408/231 |
| 5,634,933 A * | 6/1997 | McCombs | A61B 17/162 408/226 |
| 5,871,493 A * | 2/1999 | Sjostrom | A61B 17/162 604/22 |
| 5,904,687 A * | 5/1999 | Del Rio | A61B 17/162 408/231 |
| 5,921,563 A * | 7/1999 | Huggins | B23B 31/14 279/131 |
| 5,928,244 A * | 7/1999 | Tovey | A61F 2/0805 606/104 |
| 6,065,966 A * | 5/2000 | Lohn | A61B 17/162 433/128 |

(Continued)

FOREIGN PATENT DOCUMENTS

| | | |
|---|---|---|
| CN | 1780587 A | 5/2006 |
| WO | WO 1996010962 A1 | 4/1996 |

*Primary Examiner* — Eric S Gibson (57) ABSTRACT

The invention relates to an attachment mechanism for detachably coupling a first component to a second component as part of a surgical instrument. There is also provided a surgical instrument comprising the attachment mechanism.

7 Claims, 6 Drawing Sheets

A - A

(56) References Cited

U.S. PATENT DOCUMENTS

| | | | |
|---|---|---|---|
| 9,078,672 B1* | 7/2015 | Rosse | A61B 17/1631 |
| 2002/0151902 A1* | 10/2002 | Riedel | A61B 17/162 |
| | | | 606/80 |
| 2003/0023256 A1* | 1/2003 | Estes | A61B 17/162 |
| | | | 606/167 |
| 2003/0130663 A1* | 7/2003 | Walen | A61B 17/1615 |
| | | | 606/80 |
| 2003/0163134 A1* | 8/2003 | Riedel | A61B 17/162 |
| | | | 606/79 |
| 2007/0205567 A1* | 9/2007 | Eberle | A61B 17/00 |
| | | | 279/77 |
| 2009/0247901 A1 | 10/2009 | Zimmer | |
| 2009/0275858 A1 | 11/2009 | Hardin | |
| 2011/0064978 A1* | 3/2011 | McGahan | A61B 17/7091 |
| | | | 429/61 |
| 2011/0319896 A1* | 12/2011 | Papenfuss | A61B 17/1631 |
| | | | 606/79 |
| 2012/0259337 A1* | 10/2012 | del Rio | A61B 17/1615 |
| | | | 606/80 |
| 2012/0265177 A1* | 10/2012 | Beedall | A61B 17/162 |
| | | | 606/1 |
| 2013/0041377 A1* | 2/2013 | Kuntz | A61B 17/1642 |
| | | | 606/80 |
| 2013/0245704 A1* | 9/2013 | Koltz | A61B 17/00 |
| | | | 606/86 A |
| 2013/0325019 A1 | 12/2013 | Gowers | |
| 2014/0148808 A1 | 5/2014 | Atsma | |
| 2014/0207142 A1* | 7/2014 | Takeuchi | A61B 17/1617 |
| | | | 606/80 |
| 2017/0333092 A1* | 11/2017 | McGahan | A61B 17/7074 |
| 2018/0014820 A1* | 1/2018 | Garadi | A61B 17/00 |
| 2018/0064503 A1* | 3/2018 | Young | A61B 17/162 |

* cited by examiner

ATTACHMENT MECHANISM FOR A SURGICAL INSTRUMENT COMPONENT

CROSS REFERENCE TO RELATED PCT APPLICATION

This application is a National Stage 35 U.S.C. 371 of International Patent Application PCT/EP2016/052294 filed Feb. 3, 2016, which claims priority to United Kingdom Application No. 1504854.9, filed Mar. 23, 2015, both of which are incorporated by reference in their entireties.

The present invention relates to an attachment mechanism for surgical instrument components. In particular, the invention relates to an attachment mechanism that can be used to releasably attach one component to another component as part of a surgical instrument. The invention also relates to a surgical instrument comprising the attachment mechanism.

Surgical instruments often have modular components or parts that can be clipped together and which can be simply unclipped by means of a simple attachment mechanism. Examples of such components that are required to be releasably detached are reamer heads onto reamer drivers, drill bits onto drill drivers, and impaction heads on impaction handles. The attachment mechanism, for example for reamers, can be ergonomically complex while some attachment mechanisms take the form of pinch levers which engage with cooperating notches or grooves. The levers are disengaged from the notches or grooves by pinching the levers together. Where the components are stationery the use of a simple pinch lever attachment mechanism is sufficient. However, when one or both of the components is spinning it is challenging to provide pinch levers which are not only easy to access but will not be accidentally actuated and will not risk injury to the user when spinning rapidly. This can be addressed by providing rigid guards around the levers but in order to be able to actuate the levers a user has to push in between these guards which can be very awkward.

An additional problem with these attachment mechanisms is that for some surgical instruments, such as acetabular reamer drivers, the use of levers can make them difficult to clean effectively because of the presence of springs which are used to bias the levers to an open position.

In accordance with the present invention, there is provided an attachment mechanism for detachably coupling a first component to a second component as part of a surgical instrument, the attachment mechanism being provided on the first component and including first and second attachment members configured to releasably engage with a respective attachment element on the second component to detachably couple the first and second components, the attachment mechanism including a pair of actuating levers pivotably mounted on a fulcrum and moveable between a first position in which the first and second attachment members are engaged with the attachment element to couple the first and second components together and a second position in which the first and second attachment members are disengaged from the attachment element to thereby release the second component from engagement with the first component, and wherein portions of each of the first and second levers are embedded in a sleeve comprising a resiliently deformable material which allows the first and second levers to be pivotable between the first position and the second position and which provides a restoring force to the first and second levers to bias the first and second levers to the first position.

This provides the advantages of protecting the levers so that, particularly, for example, when used on a rotating drive shaft, the levers are encased and this prevents the ends of the levers from catching on soft tissue or on other pieces of equipment. There is also a potential reduction in the risk of injury. The sleeve eliminates the need for additional biasing components such as springs which makes the attachment mechanism easier to clean. Fewer components are required which provides for easier assembly and lower manufacturing costs.

The flexible sleeve may be tubular in shape. The flexible sleeve may have a frusto-conical longitudinal cross-section.

The first and second levers may be configured for manual activation so as to move from the first position to the second position. The manual activation may be in the form of a pinching movement between two fingers or a finger and thumb. Typically, this manual activation may require the application of a force of between about 10 N and about 50 N and more particularly between about 20 N and about 30 N. To provide a restoring force sufficient to bias the first and second levers to the first position, after having been manually activated to the second position, the flexible material may have a Shore A hardness of between about 40 and about 85 and more preferably between about 50 and about 70, with a thickness of between about 1 mm and about 7 mm and more preferably about 2 mm and about 5 mm.

The resiliently deformable material may be silicone. Alternatively, the resiliently deformable material could be a synthetic rubber, comprising a polymer, for example, an elastomer such as chloropene, polychloropene, nitrile rubber or polybutadiene, natural rubbers, or a thermoplastic elastomer.

The flexible sleeve may include ribbed regions congruent with the levers. These ribbed regions provide additional grip for finger tips and also provide a visual indication of the location of the first and second levers which can assist the operator. The ribbed regions can be provided in a recessed portion of the flexible sleeve.

The attachment mechanism may include a protective cover for exposed parts of the actuating levers.

The attachment members may comprise an inclined surface which is configured to engage the attachment element to move the first and second levers to the second position.

According to a further aspect of the invention there is provided a surgical instrument comprising the attachment mechanism as herein described.

Figure 1:
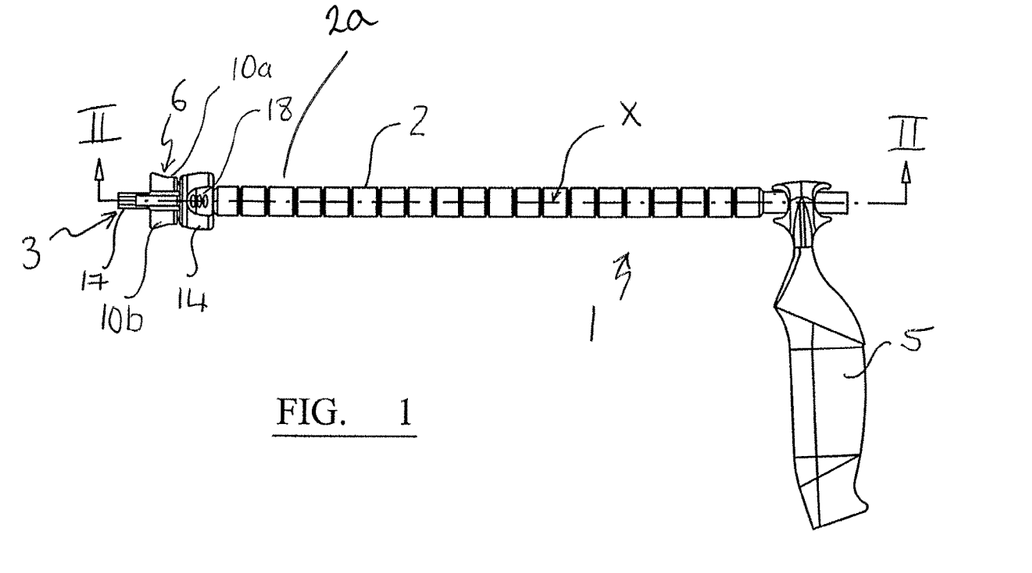
FIG. 1 is a side view of a component of surgical instrument utilising attachment mechanism of the present invention.
Figures 2, 3:
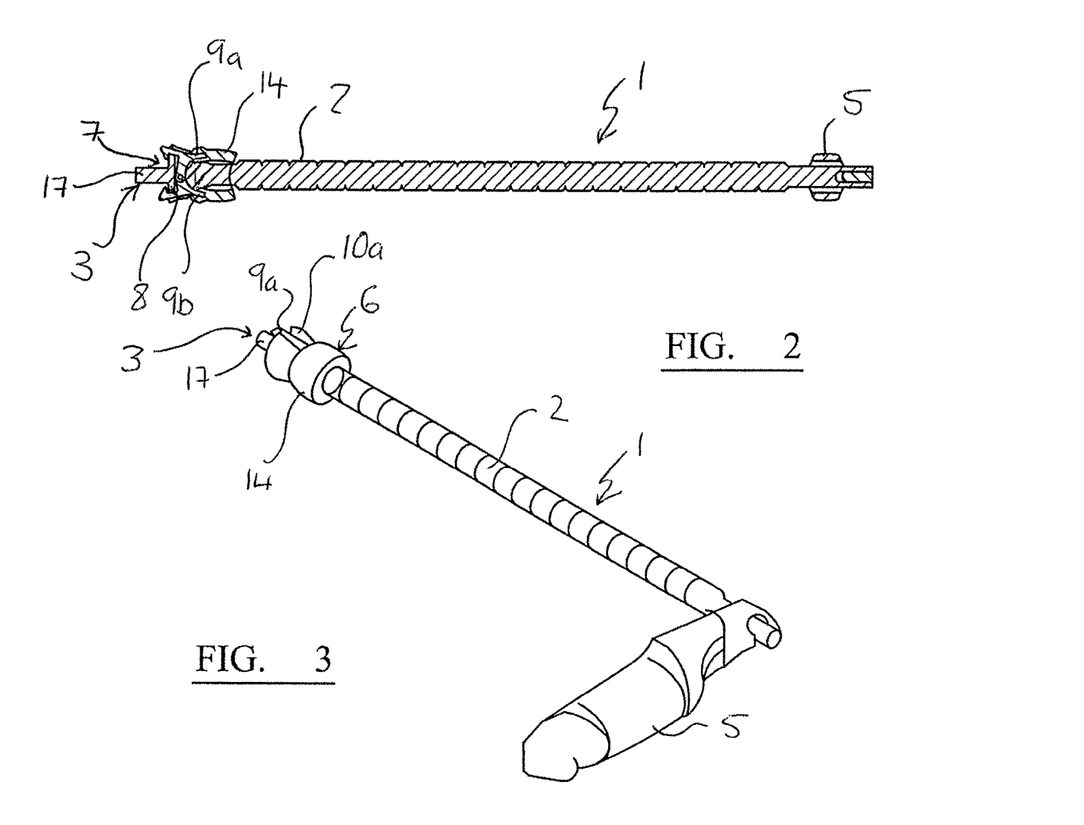
FIG. 2 is a cross-sectional view of the surgical instrument of FIG. 1 in the plane indicated by the arrows II-II in FIG. 1.
FIG. 3 is a schematic orthogonal view corresponding to FIG. 1.

Embodiments of the invention will now be described, by way of example only, and with reference to the accompanying drawings, in which:

FIG. 1 illustrates a section of a component 1 of a surgical instrument.

In this embodiment, the component 1 may be part of a reamer for orthopaedic surgery and includes an elongate shaft 2 which is connected to a rotational drive. However, it will be understood by a person skilled in the art that the component 1 can be any component or part of any surgical instrument which is required to be detachably connected to another component or part. In this regard, the elongate shaft 2 is configured to be connected to a second component 3 at a first end 2a. A handle 5 is provided.

The elongate shaft 2 has an attachment mechanism 6 at the first end 2a for attaching the elongate shaft 2 to the second component 3 by means of an attachment element 7 provided on the second component 3. The attachment element 7 of the second component 3 is therefore configured for engagement with the attachment mechanism 6 of the component 1 as will be described in more detail below.

In the embodiment described herein, the attachment element 7 on the second component 3 comprises a lip or flange 8 extending laterally of an elongate shaft 17 of the second component 3.

It will be understood that various forms and configurations of the attachment element 7 are possible, with the embodiment described herein being an example only.

The attachment mechanism 6 includes a pair of levers 9a, 9b which are pivotably mounted on a pin 4 which acts as a fulcrum. In an alternative, each lever 9a, 9b can be mounted on a separate pin spaced apart and arranged substantially parallel to each other.

The pin 4 is mounted towards the end of the elongate shaft 2 within a first bore 22 extending widthways through the elongate shaft 2 in a direction perpendicular to the longitudinal axis X of the elongate shaft 2.

Figure 6:
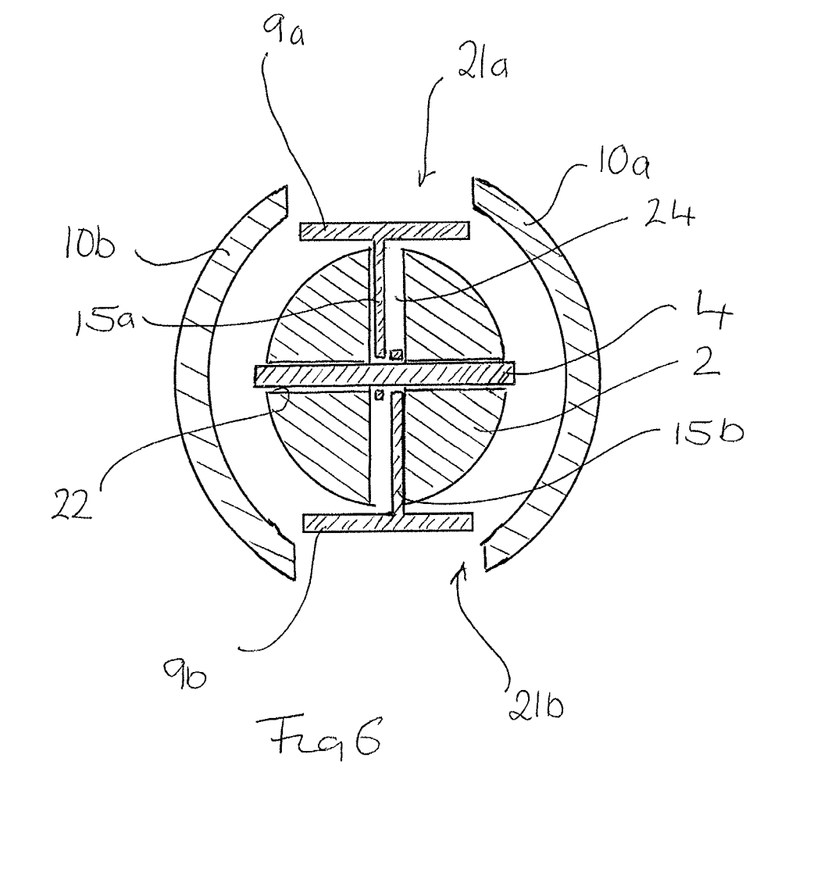
FIG. 6 is a cross-sectional view in the direction of arrows C-C of FIG. 4A.

The levers 9a, 9b are each in the form of a flat arm with a centrally located projection 15a, 15b for attachment to the pin 4. Each projection 15a, 15b has an aperture 23a, 23b through which the pin 4 is retained. The projections 15a, 15b are retained within a second bore 24 extending also widthways through the elongate shaft 2 in a direction perpendicular to the first bore 22 and the longitudinal axis X of the elongate shaft 2. This is illustrated in FIG. 6. In this way, the levers 9a, 9b are retained on the elongate shaft 2 and configured for rotation around the pin 4.

Each lever 9a, 9b has an attachment member 11a, 11b in the form of an inwardly facing lip or flange at a first end 12a, 12b of the lever 9a, 9b.

The opposite, second, ends 13a, 13b of each lever 9a, 9b are embedded in a hollow flexible sleeve 14 by overmoulding to form an adhesive/cohesive bond with the levers 9a, 9b and a hermetic seal.

The flexible sleeve is tubular with a frustoconical longitudinal cross-section. The interior of the flexible sleeve 14 defines a recess 16 which surrounds a portion of the end of the shaft 2. The flexible sleeve 14 is made from a resiliently deformable material with a Shore A hardness of between about 40 and about 85 and more preferably between about 50 and about 70, and with a thickness, t, of between about 1 mm and about 7 mm and more preferably about 2 mm and about 5 mm.

In this embodiment the resiliently deformable material used for the sleeve 14 may be silicone. Alternatively, the resiliently deformable material could be a synthetic rubber, comprising a polymer, for example, an elastomer such as chloropene, polychloropene, nitrile rubber or polybutadiene, natural rubbers, or a thermoplastic elastomer.

A pair of protective covers 10a, 10b are provided around the exposed parts of the levers 9a, 9b i.e. those parts not encased in the flexible sleeve 14. The protective covers 10a, 10b define openings 21a, 21b to enable access to the levers 9a, 9b for cleaning. The protective covers 10a, 10b also prevent the levers 9a, 9b catching surrounding tissue when they spin as the elongate shaft 2 rotates. The protective covers 10a, 10b form part of the elongate shaft 2 and are made from the same material.

To detachably connect the component 1 with the second component 3, the attachment members 11a, 11b are configured to engage with the lip or flange 8 extending laterally of an elongate shaft 17 of the second component 3 when the levers 9a, 9b are in a first position.

The resilience of the deformable material is such that the flexible sleeve 14 is biased to an open and un-deformed shape and will, when deformed, provide sufficient restoring force to return to its un-deformed configuration when there is no manual pressure applied.

As such, the levers 9a, 9b are biased to the first position by the action of the flexible and resilient sleeve 14.

The levers 9a, 9b are arranged to pivot on the pin 4 to move the first ends 12a, 12b of the levers 9a, 9b apart and together—as indicated by the double-headed arrows in FIG. 5. When the first ends 12a, 12b are apart, the levers 9a, 9b are in a second position. In the second position, the attachment members 11a, 11b are disengaged from the lip or flange 8, thus enabling the second component 3 to be detached from the component 1.

To move the levers 9a, 9b to the second position, the levers 9a, 9b are manually actuated by squeezing the second ends 13a, 13b together using a finger-thumb pinching motion.

Figure 4A:
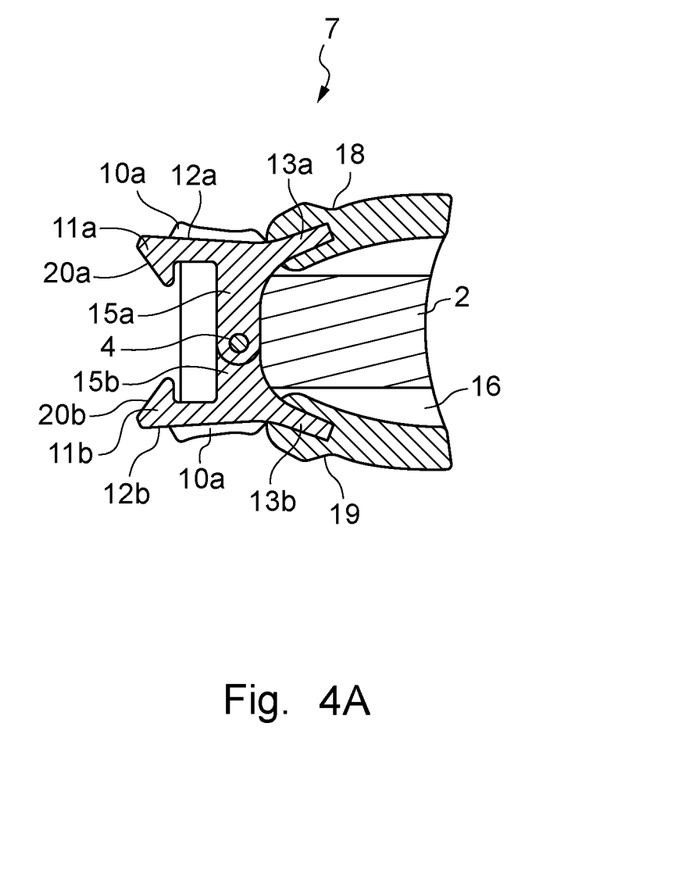
FIG. 4A is a schematic cross-sectional view of an attachment mechanism as provided on the surgical instrument of FIG. 1 showing the levers in an engaging orientation.
Figure 4B:
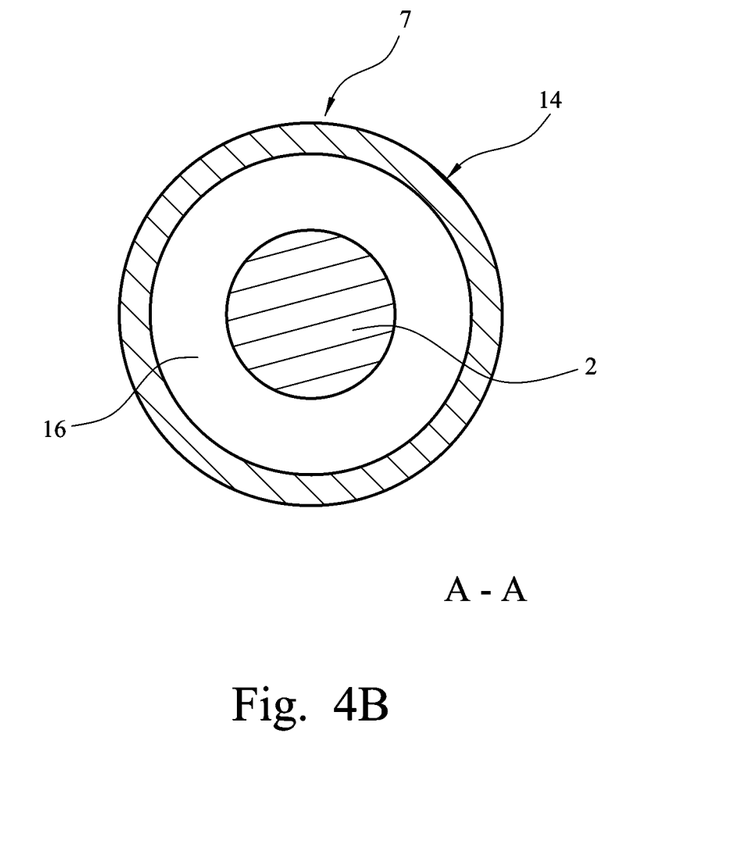
FIG. 4B is a cross-sectional view in the direction of arrows A-A of FIG. 4A.
Figure 5A:
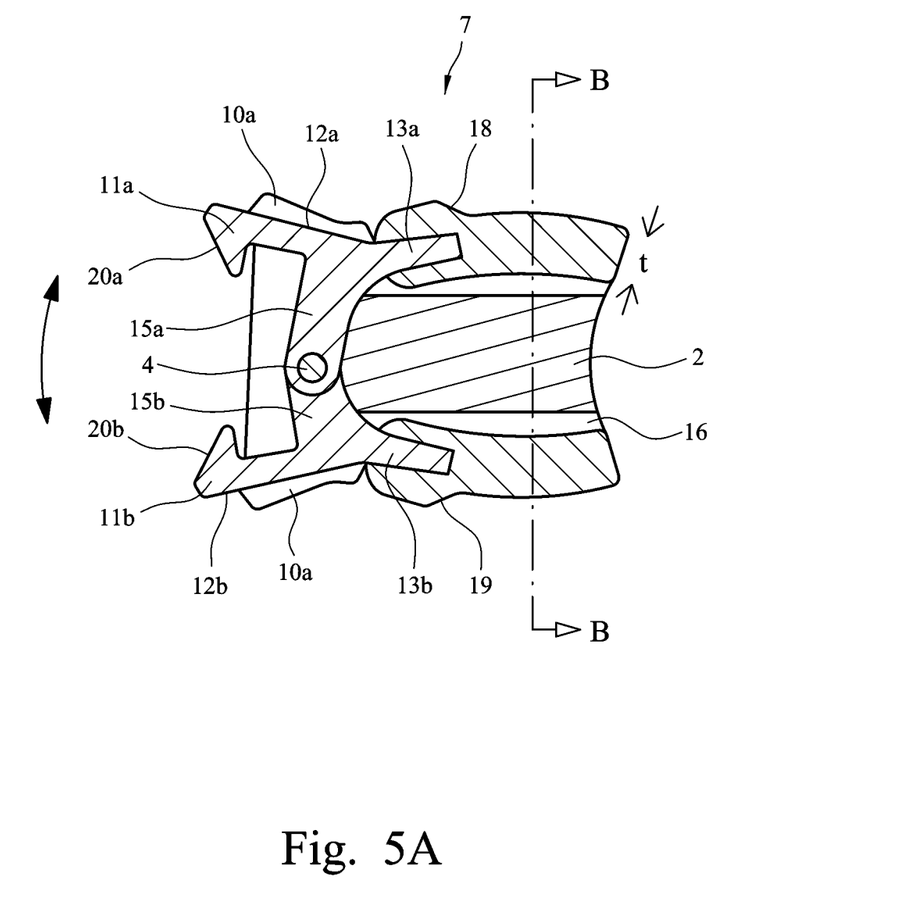
FIG. 5A is a schematic cross-sectional view of an attachment mechanism as provided on the surgical instrument of FIG. 1 showing the levers in a non-engaging orientation.

FIG. 4A illustrates the levers 9a, 9b in the first position, while FIG. 5A illustrates the levers in the second, open position.

Figure 5B:
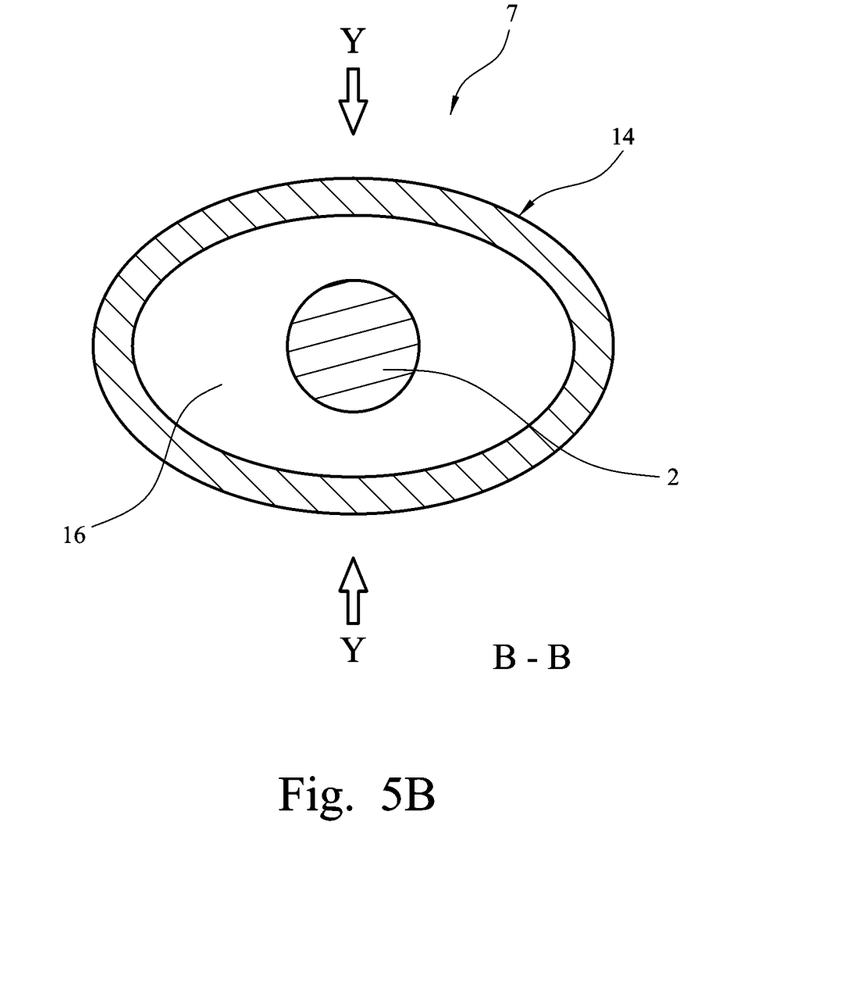
FIG. 5B is a cross-sectional view in the direction of arrows B-B of FIG. 5A.

In this way, to attach the second component 3 to the component 1, the levers 9a, 9b are manually actuated to the second position by squeezing the second ends 13a, 13b together, and inserting the attachment element 7 on the elongate shaft 17 of the second component 3 between the levers 9a, 9b. The arrows Y in FIG. 5B illustrate the direction of this squeezing action. The second ends 13a, 13b of the levers 9a, 9b are then released to enable the first ends 12a, 12b of the levers 9a, 9b to move together so that the attachment members 11a, 11b move into engagement with the lip or flange 8 of the second component 3, thereby connecting and locking the two components 1, 3 together.

As an alternative, rather than using a manual actuation of the levers 9a, 9b, the attachment element 7 can be pushed axially against the attachment members 11a, 11b of the levers 9a, 9b to force the first ends 12a, 12b apart. To facilitate this, the attachment members 11a, 11b have inclined faces 20a, 20b against which the attachment element 7 acts to force the first ends 12a, 12b apart.

The biasing of the levers 9a, 9b to the first position will then lock the two components 1, 3 together.

To disengage the two components 1, 3, the second ends 13a, 13b are pinched together, thus moving the first ends 12a, 12b apart thereby disengaging the attachment members 11a, 11b from lip or flange 8 of the attachment element 7. The second component 3 can then be removed.

To assist in the manual actuation of the levers 9a, 9b, the flexible sleeve 14 includes two curved recessed portions 18, 19 at the region where the two second ends 13a, 13b are enclosed. These recessed portions 18, 19 serve to accommodate finger tips and have ribbed regions to provide additional grips. These recessed portions 18, 19 additionally serve to provide a visual indication of the location of the levers 9a, 9b.

The invention claimed is:

1. A surgical instrument comprising:
    a first component;
    a second component; and
    an attachment mechanism, the attachment mechanism for detachably coupling the first component to the second component, the attachment mechanism being provided on the first component and including first and second attachment members configured to releasably engage with a respective attachment element on the second component to detachably couple the first and second components, the attachment mechanism including a pair of actuating levers pivotably mounted on a fulcrum and moveable between a first position wherein the first and second attachment members are engaged with the attachment element to couple the first and second components together and a second position wherein the first and second attachment members are disengaged from the attachment element to thereby release the second component from engagement with the first component, and wherein portions of each of the first and second levers are embedded in a sleeve comprising a resiliently deformable material which allows the first and second levers to be pivotable between the first position and the second position and which provides a restoring force to the first and second levers to bias the first and second levers to the first position.

2. The instrument according to claim 1, wherein the first and second components of the surgical instrument rotate during use.

3. The instrument according to claim 1, wherein a sleeve of the attachment mechanism has a frustoconical longitudinal cross-section.

4. The instrument according to claim 1, wherein the resiliently deformable material has a Shore A hardness of between 40 and 85 with a thickness of between 1 mm and 7 mm.

5. The instrument according to claim 4, wherein the resiliently deformable material has a Shore A hardness of between 50 and 70 with a thickness of between 2 mm and 5 mm.

6. The instrument according to claim 1, wherein the resiliently deformable material is silicone.

7. The instrument according to claim 1, wherein the resiliently deformable material is a rubber.

* * * * *